(12) United States Patent
Nilsson

(10) Patent No.: US 10,828,410 B2
(45) Date of Patent: Nov. 10, 2020

(54) APPARATUS FOR PERFORMING AN EXTRACORPOREAL BLOOD TREATMENT

(71) Applicant: GAMBRO LUNDIA AB, Lund (SE)

(72) Inventor: Anders Nilsson, Sodra Sanby (SE)

(73) Assignee: Gambro Lundia AB, Lund (SE)

( * ) Notice: Subject to any disclaimer, the term of this patent is extended or adjusted under 35 U.S.C. 154(b) by 433 days.

(21) Appl. No.: 15/575,109

(22) PCT Filed: May 23, 2016

(86) PCT No.: PCT/EP2016/061570
§ 371 (c)(1),
(2) Date: Nov. 17, 2017

(87) PCT Pub. No.: WO2016/188952
PCT Pub. Date: Dec. 1, 2016

(65) Prior Publication Data
US 2018/0147335 A1    May 31, 2018

(30) Foreign Application Priority Data

May 25, 2015  (SE) .................................... 1550668

(51) Int. Cl.
*A61M 1/16* (2006.01)
*G01R 19/22* (2006.01)
(Continued)

(52) U.S. Cl.
CPC ........ *A61M 1/1607* (2014.02); *A61M 1/3406* (2014.02); *A61M 1/3413* (2013.01);
(Continued)

(58) Field of Classification Search
CPC .............. A61M 1/1617; A61M 1/3406; A61M 1/3413; A61M 1/267; A61M 1/301;
(Continued)

(56) References Cited

U.S. PATENT DOCUMENTS

| 4,508,622 A | 4/1985 | Polaschegg et al. |
| 5,567,320 A | 10/1996 | Goux et al. |

(Continued)

FOREIGN PATENT DOCUMENTS

| CN | 1747755 A | 3/2006 |
| CN | 102378636 A | 3/2012 |

(Continued)

OTHER PUBLICATIONS

Chinese First Office Action issued in related Chinese Patent Application No. 201680030741.1 dated Nov. 15, 2019—18 Pages.
(Continued)

*Primary Examiner* — Philip R Wiest
(74) *Attorney, Agent, or Firm* — K&L Gates LLP

(57) ABSTRACT

An extracorporeal blood treatment apparatus is provided comprising a filtration unit (2) connected to a blood circuit (17) and to a dialysate circuit (32); a control unit (12) is configured for calculating a sodium concentration value for the blood; the estimation of the sodium concentration includes the sub-step of calculating the sodium concentration value as an algebraic sum of a main contribution term based on the isoconductive sodium concentrate and of an offset contribution term based on a concentration of at least a substance in the dialysis fluid chosen in the group including bicarbonate, potassium, acetate, lactate, citrate, magnesium, calcium, sulphate and phosphate.

19 Claims, 1 Drawing Sheet

(51) Int. Cl.
*G01R 19/00* (2006.01)
*A61M 1/34* (2006.01)
*G01N 27/04* (2006.01)
*G01N 33/49* (2006.01)
*A61M 1/26* (2006.01)
*A61M 1/30* (2006.01)

(52) U.S. Cl.
CPC .............. *G01N 27/04* (2013.01); *G01N 33/49* (2013.01); *G01R 19/0023* (2013.01); *G01R 19/22* (2013.01); *G01R 19/225* (2013.01); *A61M 1/267* (2014.02); *A61M 1/301* (2014.02); *A61M 2205/3317* (2013.01); *A61M 2205/3334* (2013.01); *A61M 2205/3337* (2013.01); *A61M 2205/502* (2013.01); *A61M 2230/20* (2013.01)

(58) Field of Classification Search
CPC .. A61M 2205/3317; A61M 2205/3334; A61M 2205/3337; A61M 2230/20; G01N 27/04; G01N 33/49; G01R 19/0023; G01R 19/22; G01R 19/225
See application file for complete search history.

(56) References Cited

U.S. PATENT DOCUMENTS

| | | | |
|---|---|---|---|
| 5,744,031 | A | 4/1998 | Bene |
| 6,110,384 | A | 8/2000 | Goux et al. |
| 6,123,847 | A | 9/2000 | Bene |
| 6,126,831 | A | 10/2000 | Rainer et al. |
| 6,187,199 | B1 | 2/2001 | Rainer |
| 6,860,866 | B1 | 3/2005 | Thomas et al. |
| 7,077,819 | B1 | 7/2006 | Rainer et al. |
| 8,182,692 | B2 | 5/2012 | Gotch |
| 2008/0296226 | A1 | 12/2008 | Gotch |
| 2010/0168925 | A1 | 7/2010 | Hilgers et al. |
| 2012/0018379 | A1* | 1/2012 | Gross ............... A61M 1/16 210/647 |
| 2013/0116650 | A1 | 5/2013 | Vantard et al. |
| 2013/0274642 | A1 | 10/2013 | Orhan et al. |
| 2014/0263064 | A1 | 9/2014 | Jones et al. |

FOREIGN PATENT DOCUMENTS

| | | |
|---|---|---|
| CN | 204147333 U | 2/2015 |
| EP | 0330892 | 9/1989 |
| EP | 547025 | 6/1993 |
| EP | 920877 | 6/1999 |
| EP | 1104682 | 6/2001 |
| EP | 0547025 B2 | 6/2002 |
| EP | 1389475 | 2/2004 |
| EP | 2377563 | 10/2011 |
| EP | 2292284 B1 | 2/2014 |
| WO | 0002604 | 1/2000 |
| WO | 2010121805 | 10/2010 |
| WO | 2012127298 | 9/2012 |
| WO | 2012148781 | 11/2012 |

OTHER PUBLICATIONS

Chinese Search Report issued in related Chinese Patent Application No. 201680030741.1 dated Oct. 31, 2019—2 pages.
Chinese First Office Action issued in related Chinese Patent Application No. 201680030682.8 dated Nov. 25, 2019—13 Pages.
Chinese Search Report issued in related Chinese Patent Application No. 201680030682.8 dated Nov. 13, 2019—2 Pages.
Chinese First Office Action issued in related Chinese Patent Application No. 201680030683.2 dated Nov. 29, 2019—12 Pages.
Goureau Y., et al. "Evaluation of Plasma Sodium Concentration During Hemodialysis by Computerization of Dialysate Conductivity," vol. 36, No. 3, Jul. 1, 1990.
International Search Report issued in international Patent Application No. PCT/EP2016/061570 dated Aug. 19, 2016.
Written Opinion issued in international Patent Application No. PCT/EP2016/061570 dated Aug. 19, 2016.
Lauer et al., "Sodium Fluxes during hemodialysis," Trans Am Soc Artif Intern Organs (1983) vol. 29, pp. 684-687.
Swedish Patent Office Search Report issued in Appl. No. 1550667-8 dated Nov. 30, 2015.

* cited by examiner

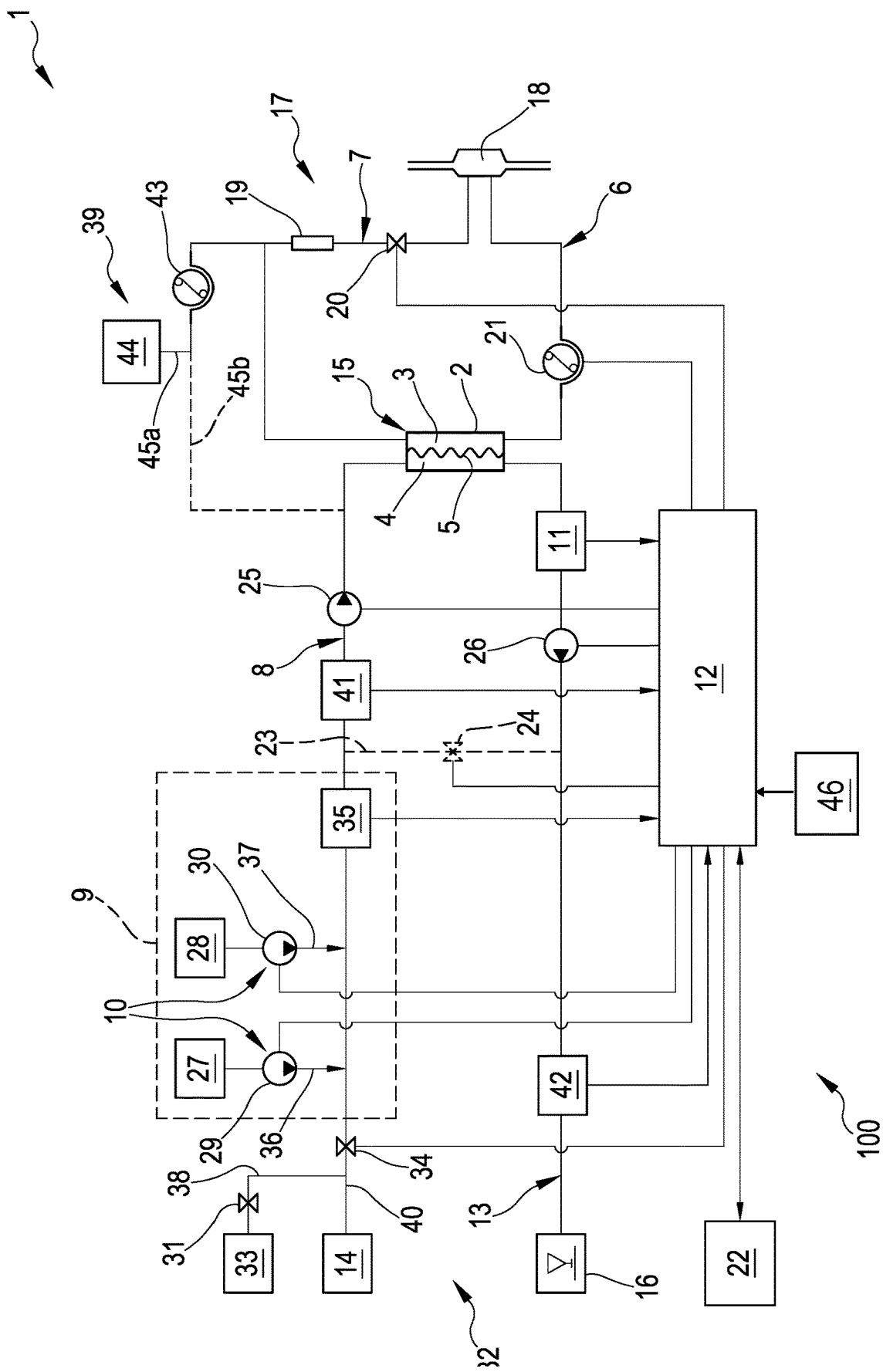

APPARATUS FOR PERFORMING AN EXTRACORPOREAL BLOOD TREATMENT

PRIORITY CLAIM

The present application is a National Phase of International Application No. PCT/EP2016/061570, filed May 23, 2016, which claims priority to Swedish Patent Application No. 1550668-6, filed May 25, 2015, the entire contents of each of which are incorporated herein by reference and relied upon.

TECHNICAL FIELD

The present invention relates to an apparatus for extracorporeal blood treatment and a method for estimating a blood parameter in an extracorporeal blood treatment apparatus.

In particular, the invention may allow determining a blood parameter (e.g. plasma sodium) during a hemodialysis or hemodiafiltration treatment through post-dialyzer conductivity measurements.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts.

In individuals who have lost the use of their kidneys, since these excretion and regulation mechanisms no longer work, the body accumulates water and waste from the metabolism and exhibits an excess of electrolytes, as well as, in general, acidosis, the pH of the blood plasma shifting downwards, below 7.35 (the blood pH normally varies within narrow limits of between 7.35 and 7.45).

In order to overcome renal dysfunction, resort is conventionally made to a blood treatment involving extracorporeal circulation through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side.

Furthermore, a pressure difference is created between the two compartments of the dialyzer which are delimited by the semipermeable membrane, so that a fraction of the plasma fluid passes by ultrafiltration through the membrane into the compartment containing the dialysis liquid.

The blood treatment which takes place in a dialyzer as regards waste from the metabolism and electrolytes results from two mechanisms of molecular transport through the membrane.

On the one hand, the molecules migrate from the liquid where their concentration is higher to the liquid where their concentration is lower. This is diffusive transport.

On the other hand, certain catabolites and certain electrolytes are entrained by the plasma fluid which filters through the membrane under the effect of the pressure difference created between the two compartments of the exchanger. This is convective transport.

Three of the abovementioned functions of the kidney, namely the removal of water, the excretion of catabolites and the regulation of the electrolytic concentration of the blood, are therefore performed in a conventional blood treatment device by the combination of dialysis and blood filtration (this combination is referred to as hemodialysis).

Some known dialysis machines offer options for both ultrafiltration and sodium profiling with an attempt to improve tolerance for ultrafiltration as dialysis session time became shorter. Indeed reduced dialysis time is associated to an increase in patient intolerance for the consequent higher UF rate.

In simple terms, the UF rate is varied so to favor improved vascular refilling. Moreover, the sodium content of the dialysis fluid is varied during the course of the treatment to directly influence plasma sodium levels. The intent is to control the rate at which sodium leaves the bloodstream into the dialysate.

There can be negative consequences to a high dialysate sodium concentration. Sodium can accumulate in the patient leading to an increased post-dialysis thirst, increased interdialytic weight gain and the development of hypertension. Sodium profiling was developed to achieve the benefits of high plasma sodium levels while at the same time avoiding unnecessary high intradialytic sodium uptake by the patient with the associated risk of sodium loading. The idea is to minimize intradialytic side-effects while removing the amount of sodium necessary to avoid sodium overload.

A normal sodium value post dialysis can be reached for hyper- or hyponatremic patients. However, monitoring of the patient's clinical status will indicate if post dialysis normonatremia is indicated. For example, hypernatremic patients often stabilize at a sodium level that is higher than the post dialysis level and may suffer side effects if hyponatremic dialysis is conducted with the intention of lowering their sodium levels.

In the above described situation a need to properly estimate and to continuously know and control the plasma sodium arises.

It is known from document U.S. Pat. No. 5,100,554 to Polaschegg a method for the in-vivo determination of hemodialysis parameters. To carry out hemodialysis with the greatest efficiency and safety, it is necessary to know the dialysis dose which depends on the clearance of the filtration unit. To be able to determine the same in vivo, the invention provides a method in which the electrolyte transfer of the dialysis fluid is measured by means of a conductivity meter at two different predetermined dialysis fluid ion concentrations and both the dialysance and plasma conductivity are determined on the basis thereof.

Document EP547025 to Sternby teaches a method for determining a concentration of sodium in the blood of a patient undergoing a dialysis treatment in an artificial kidney and/or the actual dialysance for sodium of the artificial kidney. The artificial kidney comprises an extracorporeal blood circuit connected to a filtration unit with a semipermeable membrane delimiting a first compartment for the circulation of blood on one side of the membrane and a second compartment for circulating the dialysis fluid; the method includes the steps of circulating successively in the second compartment of the filtration unit a first and a second dialysis liquid having different concentrations of sodium, measuring in the first and second dialysis liquids the conductivity upstream and downstream of the filtration unit, and calculating from the measured conductivity in the first and second dialysis fluids, the conductivity of the blood at the inlet of the filtration unit and/or the actual dialysance of the artificial kidney.

In particular, the conductivity of the blood and the actual dialysance is calculated according to the formula:

$$\kappa_{d\ out} = \kappa_{d\ in}(\kappa_{b\ in} - \kappa_{d\ in}) \times D/Q_d$$

wherein $\kappa_{d\ in}$ conductivity of the dialysis liquid upstream of the filtration unit;

$\kappa_{d\ out}$=conductivity of the dialysis liquid downstream of the filtration unit;

$\kappa_{b\ in}$=conductivity of the blood upstream of the filtration unit;

D=dialysance of the artificial kidney for conductivity;

$Q_d$=flow rate of the dialysis liquid.

EP658352, EP920877, and EP1108438 describe further improvements of the above described method for plasma conductivity calculation.

The basic principle of the above described monitoring systems is the continuous measurement of the outlet dialysate conductivity when the inlet dialysate conductivity is changed for about 1 mS/cm during two minutes. This measurement can be programmed to take place every e.g. 15, 30, 45 or 60 minutes.

The mathematical outlet conductivity modeling allows the calculation of two dialysis process parameters, namely plasma conductivity and effective ionic dialysance or ionic clearance Plasma conductivity is the reflection of the amount of electrolytes, such as sodium and other physiologically acceptable ions, in the patient. This enables to determine if patients will leave the clinic overloaded with sodium.

Notwithstanding the use of the above identified methods is today largely spread, there are still outstanding problems to give the blood property result a physiological meaning.

Strictly the "plasma conductivity" not only measure an unambiguous blood property but it is strongly influenced by the measurement itself. Generally it is assumed that if the conductivity in fluid entering the filtration unit is equal to the conductivity leaving the filtration unit will represent an unambiguous blood property.

However this is an approximation and it is almost impossible to verify correctness of the calculation by taking and measuring samples of the blood. In the past, there have been attempts to statistically connect plasma conductivity to plasma sodium, but the spread in data is large.

SUMMARY

An aim of the present invention is providing an extracorporeal blood treatment apparatus capable to properly estimate a blood parameter in the extracorporeal blood.

In detail it is an aim of the present invention to provide an extracorporeal blood treatment apparatus with a proper tool for estimating a concentration of at least a substance in the blood or a concentration-related parameter of at least a substance in the blood A further aim of the invention is to make available an extracorporeal blood treatment apparatus provided with a simple model of the ion transports in the filtration unit that contribute to conductivity change. The mathematical model allows the calculation of the plasma sodium from the conductivity measurements once known or estimated the blood values of some electrolytes.

It is an auxiliary aim of the invention to provide an extracorporeal blood treatment machine configured to automatically perform a proper automatic setting of the dialysis fluid conductivity based on the determined blood parameter.

A further auxiliary aim of the invention is to make available a dialysis apparatus able to provide an automated delivery and control of the dialysis prescription, particularly in order to restore at each dialysis session the proper sodium-water equilibrium to the patient.

At least one of the above-indicated aims is attained by an apparatus and a corresponding method as in one or more of the appended claims, taken singly or in any combination.

According to a first independent aspect of the invention an extracorporeal blood treatment apparatus is provided including:
- a filtration unit (2) having a primary chamber (3) and a secondary chamber (4) separated by a semi-permeable membrane (5);
- a blood withdrawal line (6) connected to an inlet of the primary chamber (3),
- a blood return line (7) connected to an outlet of the primary chamber (3), said blood lines being configured for connection to a patient cardiovascular system;
- a dialysis supply line (8), optionally connected to an inlet of the secondary chamber (4) for circulating a dialysis fluid;
- a dialysis effluent line (13) connected to an outlet of the secondary chamber (4);
- a control unit (12) programmed for receiving a value of a first parameter representative of an isoconductive dialysis, the first parameter being chosen in the group including a concentration of at least a substance, a concentration related parameter of at least a substance, a conductivity or a conductivity related parameter, wherein said control unit (12) is configured for:
calculating the value of a second parameter, said second parameter being chosen in a group including a concentration of at least a substance in the blood and a concentration-related parameter of at least a substance in the blood; wherein the step of calculating the value of the second parameter is performed as a function of a main contribution term based on the first parameter and as a function of an offset contribution term based on a concentration of at least a substance in the dialysis fluid chosen in the group including bicarbonate, potassium, acetate, lactate, citrate, magnesium, calcium, sulphate, and phosphate; and optionally,
storing said parameter value in a memory (46) connected to the control unit (12).

In a further independent aspect, an apparatus for extracorporeal blood treatment is provided comprising:
- a filtration unit (2) having a primary chamber (3) and a secondary chamber (4) separated by a semi-permeable membrane (5);
- a blood withdrawal line (6) connected to an inlet of the primary chamber (3),
- a blood return line (7) connected to an outlet of the primary chamber (3), said blood lines being configured for connection to a patient cardiovascular system;
- a dialysis effluent line (13) connected to an outlet of the secondary chamber (4);
- a control unit (12) programmed for receiving a value of a first parameter representative of an isoconductive dialysis, the first parameter being chosen in the group including a concentration of at least a substance, a concentration related parameter of at least a substance, a conductivity or a conductivity related parameter, wherein said control unit (12) is configured for:

calculating the value of a second parameter of the blood, said second parameter being chosen in a group including a concentration of at least a substance in the blood and a concentration-related parameter of at least a substance in the blood; wherein the calculating the parameter value is performed as a function of a main contribution term based on the first parameter and as a function of an offset contribution term based on a concentration of at least a substance in the blood chosen in the group including bicarbonate, potassium, acetate, lactate, citrate, magnesium, calcium, sulphate, and phosphate; and optionally, storing said second parameter value in a memory (46) connected to the control unit (12), in particular the parameter value being the plasma sodium concentration.

In a further independent aspect a method for estimating a blood parameter in an apparatus for extracorporeal blood treatment is provided, the apparatus comprising:

a filtration unit (2) having a primary chamber (3) and a secondary chamber (4) separated by a semi-permeable membrane (5);

a blood withdrawal line (6) connected to an inlet of the primary chamber (3), a blood return line (7) connected to an outlet of the primary chamber (3), said blood lines being configured for connection to a patient cardiovascular system;

a dialysis supply line (8), optionally connected to an inlet of the secondary chamber (4) for circulating a dialysis fluid;

a dialysis effluent line (13) connected to an outlet of the secondary chamber (4);

a control unit (12) programmed for receiving a value of a first parameter representative of an isoconductive dialysis, the first parameter being chosen in the group including a concentration of at least a substance, a concentration related parameter of at least a substance, a conductivity or a conductivity related parameter, the method comprising the following steps performed by the control unit:

calculating the value of a second parameter of the blood, said second parameter being chosen in a group including a concentration of at least a substance in the blood and a concentration-related parameter of at least a substance in the blood; wherein the step of calculating the value of the second parameter is performed as a function of a main contribution term based on the first parameter and as a function of an offset contribution term based on a difference, in particular a weighted difference, in concentration of at least a substance in the dialysis fluid and the same substance in the blood plasma; and optionally, storing said second parameter value in a memory (46) connected to the control unit (12).

In a $2^{nd}$ aspect according to the previous aspects, the control unit is configured to calculate the offset contribution term based on the concentration of two or more substances in the dialysis fluid chosen in the group including bicarbonate, potassium, acetate, lactate, citrate, magnesium, calcium, sulphate, and phosphate, in particular as a function of the concentration of at least three of said substances, optionally as a function of the concentration of bicarbonate, potassium, acetate, and citrate in the dialysis fluid.

In a $3^{rd}$ aspect according to the previous aspects, the control unit is configured to calculate the offset contribution term as a function of the difference, in particular a weighted difference, in concentration of at least a substance in the dialysis fluid and the same substance in the blood plasma.

In a $4^{th}$ aspect according to the previous aspects, the control unit is configured to calculate the offset contribution term as a function of the difference, in particular a weighted difference, in concentration of at least a substance in the dialysis fluid and the same substance in the plasma, said substance being chosen in the group including bicarbonate, potassium, acetate, lactate, and citrate, in particular as a function of the difference, in particular a weighted difference, in concentration of at least two of said substances, optionally as a function of the difference, in particular a weighted difference, in concentration of bicarbonate, potassium, and acetate in the dialysis fluid and plasma, even more optionally as a function of the difference, in particular a weighted difference, in concentration of bicarbonate, potassium, citrate, and acetate in the dialysis fluid and plasma.

In a $5^{th}$ aspect according to the previous aspects, the value representative of the isoconductive dialysis is chosen in the group including a concentration of at least a substance in the dialysis fluid, a concentration related parameter of at least a substance in the dialysis fluid, a dialysis fluid conductivity, a dialysis fluid conductivity related parameter, a plasma conductivity or a plasma conductivity related parameter, in particular the first parameter is an isoconductive sodium concentration or an isoconductive sodium concentration-related parameter.

In a $6^{th}$ aspect according to the previous aspects, the second parameter is the concentration of at least a substance in the blood, said substance being in particular sodium.

In a $7^{th}$ aspect according to the previous aspects, the first parameter is the isoconductive sodium concentration and the second parameter is the sodium concentration in the blood.

In a $8^{th}$ aspect according to the previous aspects, the main contribution term is dimensionally a concentration of a substance in a fluid.

In a $9^{th}$ aspect according to the previous aspect, the main contribution term is a concentration value which if used as a dialysis fluid concentration of sodium would run an isoconductive dialysis.

In a $10^{th}$ aspect according to the previous aspects, the main contribution term affects the second parameter for at least 80% of the second parameter value, the offset contribution term contributes to the second parameter for less than 20% of the second parameter value.

In a $11^{th}$ aspect according to the previous aspects, the sub-step of calculating the second parameter value as a function of the main contribution term and the offset contribution term is a sub-step of calculating an algebraic sum, particularly a weighted algebraic sum, of at least the main contribution term and the offset contribution term and particularly wherein the offset contribution term is dimensionally a concentration of a substance in a fluid.

In a $12^{th}$ aspect according to the previous aspects, the main contribution term affects the second parameter for at least 90% of the second parameter value, the offset contribution term contributing to the second parameter for less than 10% of the second parameter value.

In a $13^{th}$ aspect according to the previous aspects, the apparatus includes a preparation device (9) for preparing a dialysis fluid connected to said supply line (8) and comprising regulating means (10) for regulating the composition of the dialysis fluid, the regulating means (10) being connected to the control unit (12).

In a 14th aspect according to the previous aspect, the control unit (12) is configured for setting a third parameter value for the dialysis fluid in the dialysis supply line (8) at a set point, said third parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid.

In a $15^{th}$ aspect according to the previous $13^{th}$ aspect, the control unit (12) is configured for determining a profile in time for a third parameter value for the dialysis fluid in the dialysis supply line (8), said third parameter of the dialysis fluid being at least one chosen in a group including a conductivity of the dialysis fluid, a conductivity-related parameter of the dialysis fluid, a concentration of at least a substance in the dialysis fluid and a concentration-related parameter of at least a substance in the dialysis fluid; wherein the control unit drives the regulating means (10) for regulating the conductivity or the concentration of at least a substance in the dialysis fluid, the profile in time for the third parameter being based on the second parameter.

In a $16^{th}$ aspect according to anyone of the previous aspects, the control unit drives regulating means (10) for regulating the conductivity or the concentration of at least a substance in the dialysis fluid.

In a $17^{th}$ aspect according to the previous four aspects, the control unit setting the third parameter value for the dialysis fluid in the dialysis supply line (8) at the set point which is based on the second parameter.

In a $18^{th}$ aspect according to the previous aspect, the regulating means (10) regulates the concentration of at least a substance in the dialysis fluid, in particular a ionic substance, such as sodium.

In a $19^{th}$ aspect according to the previous aspect, the control unit drives the regulating means (10) for regulating the sodium concentration in the dialysis fluid to set the parameter value for the dialysis fluid in the dialysis supply line (8) at the calculated second parameter value.

In a $20^{th}$ aspect according to anyone of the previous aspects, the control unit is configured to calculate the offset contribution term as a function of the molar conductivities of at least a substance in the dialysis fluid chosen in the group including sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$), in particular as a function of the molar conductivities of at least two of said substances, in more detail as a function of the molar conductivities of at least three of said substances, optionally as a function of the molar conductivities of at least three substances chosen in the group including sodium bicarbonate ($NaHCO_3$), sodium chloride (NaCl), sodium acetate ($NaCH_3COO$), trisodium citrate ($Na_3C_6H_5O_7$), and potassium chloride (KCl).

In a $21^{st}$ aspect according to anyone of the previous aspects, the control unit is configured to calculate the offset contribution term as a function of a difference between two molar conductivities.

In a $22^{nd}$ aspect according to anyone of the previous aspects, the control unit is configured to calculate the offset contribution term as a function of a difference between a first molar conductivity of a substance chosen in the group including sodium bicarbonate ($NaHCO_3$), sodium acetate ($NaCH_3COO$), trisodium citrate ($Na_3C_6H_5O_7$), sodium lactate ($NaC_3H_5O_3$), potassium chloride (KCl), and a molar conductivity of sodium chloride (NaCl).

In a $23^{rd}$ aspect according to anyone of the previous aspects, the control unit is configured to calculate the offset contribution term as a function of a difference between a molar conductivity of sodium bicarbonate ($NaHCO_3$), and a molar conductivity of sodium chloride (NaCl).

In a $24^{th}$ aspect according to anyone of the previous aspects, the control unit is configured to calculate the offset contribution term as a function of a difference between a molar conductivity of sodium acetate ($NaCH_3COO$), and a molar conductivity of sodium chloride (NaCl).

In a $25^{th}$ aspect according to anyone of the previous aspects, the control unit is configured to calculate the offset contribution term as a function of a molar conductivity of potassium chloride (KCl).

In a $26^{th}$ aspect according to the previous aspects, the control unit is configured to calculate the offset contribution term as a function of an estimated or measured plasma water concentration of at least a substance chosen in the group including bicarbonate, potassium, acetate, lactate, and citrate, in particular as a function of the estimated or measured plasma water concentration of at least two of said substances, in more detail as a function of the estimated plasma water concentration of at least three of said substances, optionally as a function of the estimated plasma water concentration of bicarbonate, potassium, citrate, and acetate.

In a $27^{th}$ aspect according to the previous aspect, the estimated plasma water concentration of at least a substance chosen in the group including bicarbonate, potassium, citrate, and acetate is the mean pre-dialysis values of the corresponding substance for large patient populations or historical data of the corresponding substance for the individual patient or theoretical values of the corresponding substance or measured values of the corresponding substance.

In a $28^{th}$ aspect according to the previous aspects $26^{th}$ and $27^{th}$, the estimated plasma water concentration is adjusted by a respective fixed adjusting factor taking account of the Donnan effect.

In a $29^{th}$ aspect according to the previous aspects, the control unit is configured to calculate the offset contribution term as an algebraic sum of at least two components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma.

In a $30^{th}$ aspect according to the previous aspects, the control unit is configured to calculate the offset contribution term as an algebraic sum of at least three components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, the third component being function of the difference, in particular a weighted difference, in concentration of at least a third substance in the dialysis fluid and the same third substance in the blood plasma, optionally a fourth component being function of the difference, in particular a weighted difference, in concentration of at least a fourth substance in the dialysis fluid and the same fourth substance in the blood plasma.

In a $31^{st}$ aspect according to the previous aspects, the control unit is configured to calculate the offset contribution term as an algebraic sum of at least two components, a first component being function of a concentration of at least a substance in the dialysis fluid and/or in the blood plasma, a second component being function of a concentration of at least a second substance in the dialysis fluid and/or in the blood plasma.

In a 32$^{nd}$ aspect according to the previous aspects, the control unit is configured to calculate the offset contribution term as an algebraic sum of at least three components, a first component being function of a concentration of at least a substance in the dialysis fluid and/or in the blood plasma, a second component being function of a concentration of at least a second substance in the dialysis fluid and/or in the blood plasma, a third component being function of a concentration of at least a third substance in the dialysis fluid and/or in the blood plasma, optionally a fourth component being function of a concentration of at least a fourth substance in the dialysis fluid and/or in the blood plasma.

In a 33$^{rd}$ aspect according to the previous aspects 29$^{th}$ to 32$^{nd}$, said substance is an ion chosen in the group including bicarbonate anions ($HCO_3$), acetate anions ($CH_3COO$), citrate, and potassium ions ($K^+$).

In a 34$^{th}$ aspect according to the previous aspects, the control unit is configured to calculate the offset contribution term as a function of at least one flow rate, in particular the dialysate flow rate at the outlet of the secondary chamber (4).

In a 35$^{th}$ aspect according to the previous aspects, the control unit is configured to calculate the offset contribution term as a function of at least an efficiency parameter of the filtration unit (2), in particular a clearance of the filtration unit (2), optionally the urea clearance.

In a 36$^{th}$ aspect according to the previous aspects, the control unit is configured to calculate the offset contribution term as a function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a 37$^{th}$ aspect according to the previous aspects, the control unit is configured to calculate the offset contribution term as an algebraic sum of at least two, and particularly three or four or five, components, a component being function of at least a ratio between one flow rate, in particular the dialysate flow rate at the outlet of the secondary chamber (4), and an efficiency parameter of the filtration unit (2), in particular a clearance of the filtration unit (2), optionally the urea clearance.

In a 38$^{th}$ aspect according to the previous aspects, the control unit (12) is programmed for calculating said first parameter value.

In a 39$^{th}$ aspect according to the previous aspects, the control unit (12) is programmed for receiving as an external input said first parameter value.

In a 40$^{th}$ aspect according to the previous aspects, the control unit (12) is programmed for storing in a memory (46) said first parameter value, said first parameter value being not calculated by the control unit.

In a 41$^{st}$ aspect according to the previous aspects, the offset contribution term has a negative value.

In a 42$^{nd}$ aspect according to the previous aspects, the offset contribution term is a function of a rest term ($K_{rest}$), said rest term being a conductivity contribution from lesser solutes, in particular said lesser solutes being different from sodium, potassium, bicarbonate, and acetate, optionally said lesser solutes being different from sodium, potassium, citrate, bicarbonate, and acetate.

In a 43$^{rd}$ aspect according to the previous aspects, the offset contribution term is:

$$c_{di,Na,offset} = -\frac{1}{M_{\kappa,NaCl}} * [(M_{\kappa,NaHCO_3} - M_{\kappa,NaCl}) * (\alpha^{-1} * c_{pw,HCO_3} - c_{d,HCO_3}) + M_{\kappa,KCl} * (\alpha * c_{pw,K} - c_{d,K}) + (M_{\kappa,NaAc} - k) * (\alpha^{-1} * c_{pw,Ac} - c_{d,Ac})]$$

wherein:

| | |
|---|---|
| $c_{di,Na,offset}$ | is the offset contribution term |
| $M_{\kappa,NaHCO_3}$ | is the molar conductivity of sodium bicarbonate ($NaHCO_3$) |
| $M_{\kappa,NaCl}$ | is the molar conductivity of sodium chloride (NaCl) |
| $M_{\kappa,NaAc}$ | is the molar conductivity of sodium acetate ($NaCH_3COO$) |
| $M_{\kappa,KCl}$ | is the molar conductivity of potassium chloride (KCl) |
| $c_{d,HCO_3}$ | is the dialysis fluid concentration of bicarbonate ($HCO_3^-$) |
| $c_{d,K}$ | is the dialysis fluid concentration of potassium ($K^+$) |
| $c_{d,Ac}$ | is the dialysis fluid concentration of acetate ($CH_3COO^-$) |
| $c_{pw,HCO_3}$ | is the estimated or measured pre-dialysis concentration of bicarbonate ($HCO_3^-$) in plasma water |
| $c_{pw,Ac}$ | is the estimated or measured pre-dialysis concentration of acetate ($CH_3COO^-$) in plasma water |
| $c_{pw,K}$ | is the estimated or measured pre-dialysis concentration of potassium ($K^+$) in plasma water |
| $\alpha$ | is the Donnan effect corrective factor |

In a 44$^{th}$ aspect according to the previous aspects 1$^{st}$ to 42$^{nd}$, the offset contribution term is:

$$c_{di,Na,offset} = -\frac{1}{M_{\kappa,NaCl}} * \left[ (M_{\kappa,NaHCO_3} - M_{\kappa,NaCl}) * (\alpha^{-1} * c_{pw,HCO_3} - c_{d,HCO_3}) + M_{\kappa,KCl} * (\alpha * c_{pw,K} - c_{d,K}) + (M_{\kappa,NaAc} - M_{\kappa,NaCl}) * (\alpha^{-1} * c_{pw,Ac} - c_{d,Ac}) + \frac{Q_{do}}{K_u} * (K_{rest1}) \right]$$

wherein:

| | |
|---|---|
| $c_{di,Na,offset}$ | is the offset contribution term |
| $M_{\kappa,NaHCO_3}$ | is the molar conductivity of sodium bicarbonate ($NaHCO_3$) |
| $M_{\kappa,NaCl}$ | is the molar conductivity of sodium chloride (NaCl) |
| $M_{\kappa,NaAc}$ | is the molar conductivity of sodium acetate ($NaCH_3COO$) |
| $M_{\kappa,KCl}$ | is the molar conductivity of potassium chloride (KCl) |
| $K_{rest1}$ | is the conductivity contribution from lesser solutes |
| $c_{d,HCO_3}$ | is the dialysis fluid concentration of bicarbonate ($HCO_3^-$) |
| $c_{d,K}$ | is the dialysis fluid concentration of potassium ($K^+$) |
| $c_{d,Ac}$ | is the dialysis fluid concentration of acetate ($CH_3COO^-$) |
| $c_{pw,HCO_3}$ | is the estimated or measured pre-dialysis concentration of bicarbonate ($HCO_3^-$) in plasma water |
| $c_{pw,Ac}$ | is the estimated or measured pre-dialysis concentration of acetate ($CH_3COO^-$) in plasma water |
| $c_{pw,K}$ | is the estimated or measured pre-dialysis concentration of potassium ($K^+$) in plasma water |
| $Q_{do}$ | is the Dialysate flow rate at filtration unit outlet |
| $K_u$ | is the filtration unit clearance for urea |
| $\alpha$ | is the Donnan effect corrective factor |

In a 45$^{th}$ aspect according to the previous aspects 1$^{st}$ to 42$^{nd}$, the offset contribution term is:

$$c_{di,Na,offset} = -\frac{1}{M_{\kappa,NaCl}} * \left[ (M_{\kappa,NaHCO_3} - M_{\kappa,NaCl}) * (\alpha^{-1} * c_{pw,HCO_3} - c_{d,HCO_3}) + M_{\kappa,KCl} * (\alpha * c_{pw,K} - c_{d,K}) + (M_{\kappa,NaAc} - M_{\kappa,NaCl}) * \right.$$

-continued $$(\alpha^{-1} * c_{pw,Ac} - c_{d,Ac}) + \frac{K_{b_{Cit}}}{K_u}(M_{K_{Na_3Cit}} - 3M_{K_{NaCl}})$$

$$((0.167\alpha^{-3} + 0.125\alpha^{-2} + 0.706\alpha^{-1}) * c_{pw,Na_3Cit} - c_{d,Na_3Cit}) ++$$

$$\frac{Q_{do}}{K_u} * (K_{rest1})\Bigg]$$

wherein:

| | |
|---|---|
| $c_{di, Na, offset}$ | is the offset contribution term |
| $M_{K, NaHCO_3}$ | is the molar conductivity of sodium bicarbonate (NaHCO$_3$) |
| $M_{K, NaCl}$ | is the molar conductivity of sodium chloride (NaCl) |
| $M_{K, NaAc}$ | is the molar conductivity of sodium acetate (NaCH$_3$COO) |
| $M_{K, KCl}$ | is the molar conductivity of potassium chloride (KCl) |
| $M_{K, Na_3Cit}$ | Molar conductivity of trisodium citrate (Na$_3$C$_6$H$_5$O$_7$) |
| $K_{rest1}$ | is the conductivity contribution from lesser solutes |
| $c_{d, HCO_3}$ | is the dialysis fluid concentration of bicarbonate |
| $c_{d, K}$ | is the dialysis fluid concentration of potassium |
| $c_{d, Ac}$ | is the dialysis fluid concentration of acetate |
| $c_{d, Na_3Cit}$ | Dialysis fluid concentration of total citrate |
| $c_{pw, HCO_3}$ | is the estimated or measured pre-dialysis concentration of bicarbonate (HCO$_3^-$) in plasma water |
| $c_{pw, Ac}$ | is the estimated or measured pre-dialysis concentration of acetate (CH$_3$COO$^-$) in plasma water |
| $c_{pw, K}$ | is the estimated or measured pre-dialysis concentration of potassium (K$^+$) in plasma water |
| $C_{pw, Na_3Cit}$ | is the estimated or measured pre-dialysis concentration of total citrate in plasma water |
| $Q_{do}$ | is the Dialysate flow rate at filtration unit outlet |
| $K_u$ | is the filtration unit clearance for urea |
| $K_{b_{Cit}}$ | Filtration unit clearance for citrate; |
| $\alpha$ | is the Donnan effect corrective factor |

In a 46$^{th}$ aspect according to the previous aspects, the first parameter is a concentration of at least a substance in the dialysis fluid, said substance being in particular sodium.

In a 47$^{th}$ aspect according to the previous aspects, the first parameter is an isoconductive substance concentration.

In a 48$^{th}$ aspect according to the previous aspects, the first parameter is the plasma conductivity or the dialysis fluid conductivity in isoconductive dialysis.

In a 49$^{th}$ aspect according to the previous aspects, the first parameter is the plasma conductivity related parameter, said plasma conductivity related parameter being the dialysis fluid conductivity in isoconductive dialysis.

In a 50$^{th}$ aspect according to the previous aspects, the first parameter is the isoconductive sodium concentration related parameter, in particular the plasma conductivity or the dialysis fluid conductivity in isoconductive dialysis.

In a 51$^{st}$ aspect according to the previous aspects, the first parameter is the isoconductive sodium concentration related parameter, in particular the dialysis fluid conductivity in isoconductive dialysis, and the second parameter is the sodium concentration in the blood.

In a 52$^{nd}$ aspect according to the previous aspects, immediately after calculating an initial sodium concentration, the control unit is configured to drive the regulating means (10) to change the composition of the dialysis fluid and to set the dialysis fluid sodium to a substantially isoconductive sodium concentration.

In a 53$^{rd}$ aspect according to the previous aspect, after setting the dialysis fluid sodium to a substantially isoconductive sodium concentration, the control unit is configured to execute a second calculating step, based on a second determined initial conductivity of the dialysate and on a second corresponding conductivity of the dialysis fluid in the dialysis supply line (8), of a second estimate of the initial sodium concentration, said calculating the second estimate being performed maintaining the dialysis fluid conductivity substantially constant by an isoconductive sodium concentration setting.

In a 54$^{th}$ aspect according to the previous aspects, after calculating the second estimate of the isoconductive sodium concentration, the control unit is configured to drive the regulating means (10) to change the composition of the dialysis fluid and to set the dialysis fluid sodium concentration substantially equal to said second estimate.

In a 55$^{th}$ aspect according to the previous aspects, the control unit (12) is configured to determine the conductivity of the dialysis fluid both upstream and downstream of said filtration unit (2) for at least two successively prepared dialysates with different conductivities, particularly deriving from different concentrations of sodium.

Further characteristics and advantages of the present invention will better emerge from the detailed description that follows of at least an embodiment of the invention, illustrated by way of non-limiting example in the accompanying drawings.

BRIEF DESCRIPTION OF THE DRAWINGS

The description will now follow, with reference to the appended FIGURE provided by way of non-limiting example, in which:

FIG. 1 schematically represents an extracorporeal blood treatment apparatus made according to an illustrating embodiment.

DETAILED DESCRIPTION

FIG. 1 illustrates an extracorporeal blood treatment apparatus 1 in an embodiment of the invention.

An example of a hydraulic circuit 100 is schematically illustrated, but it is to be noted that the specific structure of the hydraulic circuit 100 is not relevant for the purposes of the present invention and therefore other and different circuits to those specifically shown in FIG. 1 might be used in consequence of the functional and design needs of each single medical apparatus.

The hydraulic circuit 100 exhibits a dialysis fluid circuit 32 presenting at least one dialysis fluid supply line 8, destined to transport a dialysis fluid from at least one source 14 towards a treatment station 15 where one or more filtration units 2, or dialyzers, operate.

The dialysis fluid circuit 32 further comprises at least one dialysis effluent line 13, destined for the transport of a dialysate liquid (spent dialysis fluid and liquid ultrafiltered from the blood through a semipermeable membrane 5) from the treatment station 15 towards an evacuation zone, schematically denoted by 16 in FIG. 1.

The hydraulic circuit cooperates with a blood circuit 17, also schematically represented in FIG. 1 in its basic component parts. The specific structure of the blood circuit is also not fundamental, with reference to the present invention. Thus, with reference to FIG. 1, a brief description of a possible embodiment of a blood circuit is made, which is however provided purely by way of non-limiting example.

The blood circuit 17 of FIG. 1 comprises a blood withdrawal line 6 designed to remove blood from a vascular access 18 and a blood return line 7 designed to return the treated blood to the vascular access 18.

The blood circuit 17 of FIG. 1 further comprises a primary chamber 3, or blood chamber, of the blood filtration unit 2, the secondary chamber 4 of which is connected to the hydraulic circuit 100.

In greater detail, the blood withdrawal line 6 is connected at the inlet of the primary chamber 3, while the blood return line 7 is connected at the outlet of the primary chamber 3.

In turn, the dialysis supply line 8 is connected at the inlet of the secondary chamber 4, while the dialysis effluent line 13 is connected at the outlet of the secondary chamber 4.

The filtration unit 2, for example a dialyzer or a plasma filter or a hemofilter or a hemodiafilter, comprises, as mentioned, the two chambers 3 and 4 which are separated by a semipermeable membrane 5, for example of the hollow-fiber type or plate type.

The blood circuit 17 may also comprise one or more air separators 19: in the example of FIG. 1 a separator 19 is included at the blood return line 7, upstream of a safety valve 20.

Of course other air separators may be present in the blood circuit, such as positioned along the blood withdrawal line 6.

The safety valve 20 may be activated to close the blood return line 7 when, for example, for security reasons the blood return to the vascular access 18 has to be halted.

The extracorporeal blood treatment apparatus 1 may also comprise one or more blood pumps 21, for example positive displacement pumps such as peristaltic pumps; in the example of FIG. 1, a blood pump 21 is included on the blood withdrawal line 6.

The apparatus of above-described embodiment may also comprise a user interface 22 (e.g. a graphic user interface or GUI) and a control unit 12, i.e. a programmed/programmable control unit, connected to the user interface.

The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing device operating, for example, in the blood circuit 17 and/or in the dialysis fluid circuit 32 and commandable between one first operating condition, in which the closing device allows a liquid to flow towards the filtration unit 2, and a second operative position, in which the closing device blocks the passage of liquid towards the filtration unit 2.

In this case, the control unit 12 may be connected to the closing device and programmed to drive the closing device to pass from the first to the second operative condition, should an alarm condition have been detected.

In FIG. 1 the closing device includes the safety valve 20 (e.g. a solenoid valve) controlled by the unit 12 as described above. Obviously a valve of another nature, either an occlusive pump or a further member configured to selectively prevent and enable fluid passage may be used.

Alternatively or additionally to the safety valve 20, the closing device may also comprise a bypass line 23 which connects the dialysis fluid supply line 8 and the dialysate effluent line 13 bypassing the filtration unit, and one or more fluid check members 24 connected to the control unit 12 for selectively opening and closing the bypass line 23. The components (bypass line 23 and fluid check members 24), which may be alternative or additional to the presence of the safety valve 20 are represented by a broken line in FIG. 1.

The check members 24 on command of the control unit close the fluid passage towards the treatment zone and connect the source 14 directly with the dialysis effluent line 13 through the bypass line 23.

Again with the aim of controlling the fluid passage towards the filtration unit 2, a dialysis fluid pump 25 and a dialysate pump 26 may be included, located respectively on the dialysis fluid supply line 8 and on the dialysate effluent line 13 and also operatively connected to the control unit 12.

The apparatus also comprises a dialysis fluid preparation device 9 which may be of any known type, for example including one or more concentrate sources 27, 28 and respective concentrate pumps 29, 30 for the delivery, as well as at least a conductivity sensor 35.

Of course other kinds of dialysis fluid preparation devices 9 might be equivalently used, having a single or further concentrate sources and/or a single or more pumps.

Since the dialysis apparatus may comprise various liquid sources (for example one or more water sources, one or more concentrate sources 27, 28, one or more sources 33 of disinfectant liquids) connected to the dialysis supply line 8 with respective delivery lines 36, 37 and 38, the apparatus may exhibit, at each delivery line, a respective check member (not all are shown) and, for example, comprising a valve member 31 and 34 and/or an occlusive pump.

The preparation device 9 may be any known system configured for on-line preparing dialysis fluid from water and concentrates.

The dialysis supply line 8 fluidly connects the preparation device for preparing dialysis fluid to the filtration unit 2. The preparation device 9 may be, for example, the one described in the U.S. Pat. No. 6,123,847 the content of which is herein incorporated by reference.

As shown, the dialysis supply line 8 connects the preparation device 9 for preparing dialysis fluid to the filtration unit 2 and comprises a main line 40 whose upstream end is intended to be connected to a source 14 of running water.

Delivery line/s 36/37 is/are connected to this main line 40, the free end of which delivery line/s is/are intended to be in fluid communication (for example immersed) in a container/s 27, 28 for a concentrated saline solution each containing sodium chloride and/or calcium chloride and/or magnesium chloride and/or potassium chloride.

Concentrate pump/s 29, 30 is/are arranged in the delivery line/s 36/37 in order to allow the metered mixing of water and concentrated solution in the main line 40. The concentrate pump/s 29, 30 is/are driven on the basis of the comparison between 1) a target conductivity value for the mixture of liquids formed where the main line 40 joins the delivery line/s 36/37, and 2) the value of the conductivity of this mixture measured by means of a conductivity sensor 35 arranged in the main line 40 immediately downstream of the junction between the main line 40 and the delivery line/s 36/37.

Therefore, as mentioned, the dialysis fluid may contain, for example, ions of sodium, calcium, magnesium, and potassium and the preparation device 9 may be configured to prepare the dialysis fluid on the basis of a comparison between a target conductivity value and an actual conductivity value of the dialysis fluid measured by the conductivity sensor 35 of the device 9.

The preparation device 9 comprises regulating means 10, of a known type (i.e. concentrate pump/s 29, 30), which is configured to regulate the concentration of a specific substance, in particular an ionic substance, in the dialysis liquid. Generally it is advantageous to control the sodium concentration of the dialysis fluid.

The dialysis supply line 8 forms an extension of the main line 40 of the preparation device 9 for preparing dialysis fluid. Arranged in this dialysis supply line, in the direction in which the liquid circulates, there are the first flow meter 41 and the dialysis fluid pump 25.

The dialysis effluent line 13 may be provided with a dialysate pump 26 and a second flow meter 42. The first and second flow meters 41, 42 may be used to control (in a known manner) the fluid balance of a patient connected to the blood circuit 17 during a dialysis session.

A sensor 11 is provided on the dialysis effluent line 13, immediately downstream the filtration unit 2, to measure a parameter value of the dialysate in the dialysate effluent line.

In detail, the parameter of the dialysate, which is measured by the sensor 11 is at least one chosen in the group consisting of conductivity of the dialysate, a conductivity-related parameter of the dialysate, concentration of at least a substance in the dialysate and a concentration-related parameter of at least a substance in the dialysate.

In detail the sensor 11 is a conductivity sensor, which is connected to the dialysis effluent line 13, and is configured to detect conductivity values of the dialysate downstream of the filtration unit 2.

Alternatively (or in combination) sensor 11 may include a concentration sensor configured for measuring the concentration of at least one substance in the dialysate, such as sodium concentration.

Correspondingly, sensor 35 on the dialysis fluid supply line may be not a conductivity sensor and, differently, may include a concentration sensor configured for measuring the concentration of at least one substance in the dialysis fluid, such as sodium concentration.

The control unit 12 of the dialysis apparatus represented in FIG. 1 may be connected to a (graphic) user interface 22 through which it may receive instructions, for example target values, such as blood flow rate $Q_b$, dialysis fluid flow rate $Q_{di}$, infusion liquid flow rate $Q_{inf}$ (where appropriate), patient weight loss WL. The control unit 12 furthermore may receive detected values by the sensors of the apparatus, such as the aforementioned flow meters 41, 42, the (e.g. conductivity) sensor 35 of the preparation device 9 and the (e.g. conductivity) sensor 11 in the dialysis effluent line 13. On the basis of the instructions received and the operating modes and algorithms which have been programmed, the control unit 12 drives the actuators of the apparatus, such as the blood pump 21, the aforementioned dialysis fluid and dialysate pumps 25, 26, and the preparation device 9.

As already mentioned, the described embodiments are intended to be non-limiting examples. In particular the circuits of FIG. 1 should not be interpreted as defining or limiting, as an apparatus such as in the invention may comprise other additional or alternative components to those described.

For example an ultrafiltration line may be included, with at least one respective pump connected to the dialysis effluent line 13.

One or more infusion lines 39 may also be included, with respective infusion pumps 43 or flow regulation valves, the infusion lines being connected up to the blood return line 7 and/or the blood withdrawal line 6 and/or directly to the patient. The liquid sources for the infusion lines may be pre-packaged bags 44 and/or liquids prepared by the apparatus itself.

In the example of FIG. 1, an infusion line 39 is shown directly connected to the blood return line 7, in particular to the air separator 19. The infusion line 39 may either receive infusion liquid from a pre-packaged bag 44 (solid line 45a) or from an online preparation trough branch 45b (dotted line).

Of course a pre-infusion line may be alternatively or additionally provided receiving the infusion liquid from a bag or from an online preparation device.

The blood circuit of FIG. 1 is intended for double needle treatments; however, this is a non-limiting example of the blood set.

Indeed, the apparatus may be configured to perform single needle treatments, i.e. the patient is connected to the extracorporeal blood circuit by way of a single needle and the extracorporeal line from the patient is then split into a withdrawal line and a return line, using, for example, an 'Y' connector. During single needle treatment, a blood withdrawal phase removing blood from patient is alternated to a blood return phase in which blood is restituted to the patient.

Furthermore one or more devices for measuring specific substance concentrations might be implemented either (or both) in the dialysis fluid side or (and) in the blood side of the hydraulic circuit. Concentration of calcium, potassium, magnesium, bicarbonate, and/or sodium might be desired to be known.

Finally, the above-cited one or more pumps and all the other necessary temperature, pressure and concentration sensors may operate either on the dialysis supply line 8 and/or on the dialysis effluent line 13, in order to adequately monitor the preparation and movement of the liquid in the hydraulic circuit.

Given the above description of a possible embodiment of extracorporeal blood treatment apparatus, thereafter the specific working of the apparatus and the algorithm programming the control unit are described.

Definitions

We define the 'dialysis fluid' as the fluid prepared and introduced to the second chamber (4) of the filtration unit (2), the dialyzer. The dialysis fluid may also be denoted "fresh dialysis fluid".

We define the 'dialysate' as the fluid from the outlet from the second chamber (4) of the filtration unit (2), the dialyzer. Dialysate is the spent dialysis fluid, comprising the uremic toxins removed from the blood.

We define 'isoconductive dialysis', as a dialysis treatment where the conductivity of the dialysis fluid does not change pre- to post-filtration unit (2), $\kappa_{di}=\kappa_{do}$.

We define 'plasma conductivity' as the conductivity of the dialysis fluid in an isoconductive dialysis.

We define 'isoconductive substance concentration' as the substance concentration in the dialysis fluid in an isoconductive dialysis.

We define 'isoconductive sodium concentration' as the sodium concentration of the dialysis fluid in an isoconductive dialysis.

In this application the term "citrate" means that the component is in form of a salt of citric acid, such as sodium, magnesium, calcium, or potassium salt thereof. The citric acid (denoted $C_6H_8O_7$) is deprotonated stepwise, therefore the "citrate" include all the different forms, citrate (denoted $C_6H_5O_7^{3-}$), hydrogen citrate (denoted $C_6H_6O_7^{2-}$), and dihydrogen citrate (denoted $C_6H_7O_7^{-}$).

The term "citrate" or "total citrate" means that the total amount of citric acid and any salts thereof, such as its sodium, magnesium, calcium, or potassium salt thereof.

In other terms, "total citrate" is the sum of free citrate ions and citrate containing complexes and ion pairs.

Glossary

The following terms are consistently used throughout the equations provided in the following description of the detailed working of the extracorporeal blood treatment apparatus.

| | | |
|---|---|---|
| $c_{di,Na,offset}$ | Offset contribution term | mmol/L |
| $M_{K,NaHCO_3}$ | Molar conductivity of sodium bicarbonate (NaHCO$_3$) | L · mS/mmol · cm |
| $M_{K,NaCl}$ | Molar conductivity of sodium chloride (NaCl) | L · mS/mmol · cm |
| $M_{K,NaAc}$ | Molar conductivity of sodium acetate (NaCH$_3$COO) | L · mS/mmol · cm |
| $M_{K,KCl}$ | Molar conductivity of potassium chloride (KCl) | L · mS/mmol · cm |
| $M_{K,Na_3Cit}$ | Molar conductivity of trisodium citrate (Na$_3$C$_6$H$_5$O$_7$) | L · mS/mmol · cm |
| $\kappa_{rest1}$ | Conductivity contribution from lesser solutes | mS/cm |
| $c_{d,HCO_3}$ | Dialysis fluid concentration of bicarbonate (HCO$_3^-$) | mmol/L |
| $c_{d,K}$ | Dialysis fluid concentration of potassium (K$^+$) | mmol/L |
| $c_{d,Ac}$ | Dialysis fluid concentration of acetate (CH$_3$COO$^-$) | mmol/L |
| $c_{d,Na_3Cit}$ | Dialysis fluid concentration of total citrate | mmol/L |
| $c_{pw,HCO_3}$ | Estimated or measured pre-dialysis concentration of bicarbonate (HCO$_3^-$) in plasma water | mmol/L |
| $c_{pw,Ac}$ | Estimated or measured pre-dialysis concentration of acetate (CH$_3$COO$^-$) in plasma water | mmol/L |
| $c_{pw,K}$ | Estimated or measured pre-dialysis concentration of potassium (K$^+$) in plasma water | mmol/L |
| $c_{pw,Na_3Cit}$ | Estimated or measured or known pre-dialysis concentration of total citrate in plasma water | mmol/L |
| $Q_{do}$ | Dialysate flow rate at filtration unit outlet | mL/min |
| $Q_{Bset}$ | Set blood flow rate | mL/min |
| $K_u$ | Filtration unit clearance for urea | mL/min |
| $K_{b,Cit}$ | Filtration unit clearance for citrate | mL/min |
| $\alpha$ | Donnan effect corrective factor | Dimensionless |
| $\kappa_{di}$ | Conductivity of the dialysis fluid upstream of the filtration unit | mS/cm |
| $\kappa_{do}$ | Conductivity of the dialysis fluid downstream of the filtration unit (dialysate) | mS/cm |
| D | Dialysance of the filtration unit | mL/min |
| $Q_d$ | Flow rate of the dialysis liquid | mL/min |
| $\kappa_{p,1}$ | Plasma conductivity first estimate | mS/cm |
| $\kappa_{0,di}$ | Dialysis fluid conductivity at the filtration unit inlet for a pure electrolyte solution | mS/cm |
| $\kappa_{0,do}$ | Dialysate conductivity at the filtration unit outlet for a pure electrolyte solution | mS/cm |
| $f_{pw}$ | Plasma water fraction, i.e., the part of plasma that is pure water | Dimensionless |
| $C_{di,Na,isocond}$ | Isoconductive sodium concentration | mmol/L |
| $\kappa_j$ | Partial conductivity for salt j | mS/cm |
| C | Concentrations | mmol/L |
| $c_{p,Na}$ | Plasma sodium concentration | mmol/L |
| $c_{pw,Na}$ | Concentration of sodium (Na$^+$) in plasma water | mmol/L |
| $c_{pw}$ | Plasma water concentration | mmol/L |
| $c_d$ | Dialysis fluid concentration | mmol/L |
| $c_{di,Na}$ | Dialysis fluid concentration of sodium at the filtration unit inlet | mmol/L |
| $c_{do,Na}$ | Dialysis fluid concentration of sodium at the filtration unit outlet | mmol/L |

The Donnan factor adjusts for electrical effects on ions assuring electroneutrality to be kept over the membrane. For estimating the Donnan factor reference is made to Trans Am Soc Artif Intern Organs, 1983; 29; 684-7, "Sodium Fluxes during hemodialysis", Lauer A., Belledonne M., Saccaggi A., Glabman S., Bosch J.

In order to implement a method for estimation of plasma sodium during hemodialysis a model of ion transport in the filtration unit has been developed. Indeed, if the blood values of some electrolytes are known or estimated, the plasma sodium may be calculated from the conductivity measurements by a simple filtration unit model.

According to the developed method a term, named $C_{di,Na,isocond}$, is the dialysis fluid isoconductive sodium concentration and a term, named $C_{di,Na,offset}$, is a term to obtain the plasma sodium concentration.

For two dialysis fluid separate settings (e.g. different conductivity and/or concentration of at least one solute), denoted with indices 1 and 2, the first term can be calculated by the expression:

$$c_{di,Na,isocond} = \frac{c_{di,Na,1} * (\kappa_{do,2} - \kappa_{di,2}) - c_{di,Na,2} * (\kappa_{do,1} - \kappa_{di,1})}{(\kappa_{do,2} - \kappa_{di,2}) - (\kappa_{do,1} - \kappa_{di,1})} \quad (I)$$

The term to obtain the plasma sodium concentration can be calculated through the expression:

$$c_{di,Na,offset} = \quad (II)$$
$$-\frac{1}{M_{K,NaCl}} * [(M_{K,NaHCO_3} - M_{K,NaCl}) * (\alpha^{-1} * c_{pw,HCO_3} - c_{d,HCO_3}) +$$
$$M_{K,KCl} * (\alpha * c_{pw,K} - c_{d,K}) +$$
$$(M_{K,NaAc} - M_{K,NaCl}) * (\alpha^{-1} * c_{pw,Ac} - c_{d,Ac})]$$

The plasma sodium relates to plasma water as:

$$C_{p,Na} = f_{pw} * c_{pw,Na} \quad (III)$$

where the plasma water fraction ($f_{pw}$) is usually about 0.93:

$$f_{pw} \approx 0.93$$

In view of the above calculations, it derives that:

$$c_{p,Na} = \frac{f_{pw}}{\alpha} * (c_{di,Na,isocond} + c_{di,Na,offset}) \quad (IV)$$

Solution Proposal

The above described model is extremely useful in determining the blood parameter of interest. Various steps of the proposed method which will be described below are intended to be performed by the control unit 12 of the extracorporeal blood treatment device 1, even if not explicitly stated.

In particular a treatment session is started, preferably, but not necessarily, as a double needle hemodialysis treatment.

The user shall input the prescription values through the user interface 22. For example the set values for total weight loss WL and total treatment time T are provided, as well as the blood flow rate $Q_b$ and the fresh dialysis flow rate $Q_{di}$.

Other parameters may be entered through the user interface, such as bag type, sodium user limits, etc.

The operator has to further input the 'bicarbonate' set before starting the treatment.

The control unit 12 receives from the prescription or, alternatively, calculates either the initial dialysis liquid conductivity or the initial concentration of at least one solute, e.g. sodium, in the dialysis liquid.

In this respect it is worth to note that, in the following detailed description, reference is made to regulating means controlling concentration of an ionic substance, in detail sodium concentration, in the preparation of the dialysis fluid so as to obtain a desired conductivity of the dialysis fluid.

However, regulating means directly regulating the overall dialysis fluid conductivity is also included in the spirit of the present description or, alternatively, regulating means modifying the concentration of a different ionic substance is included in the present description, too.

The hemodialysis or hemodiafiltration treatment is thereafter started.

The isoconductive sodium concentration is provided to the control unit 12. In more detail, the isoconductive sodium concentration may be calculated according to expression I.

Alternatively, an isoconductive sodium concentration related parameter may be provided to the control unit 12; the isoconductive sodium concentration related parameter may be the plasma conductivity. Indeed the isoconductive sodium concentration is correlated to the plasma conductivity; it is possible to derive, in a manner known to the person skilled in the art, the isoconductive sodium concentration knowing the plasma conductivity and vice versa; of course the composition of the dialysis fluid should be known. Indeed, the conductivity of a solution may be calculated as a sum of terms; each term represents a salt contained in the solution and each term is constructed as the product of the molar conductivity and concentration of the salt. The concentration of sodium may be calculated from conductivity from the same relation. In such a case the plasma conductivity (subsequently used to obtain the isoconductive sodium concentration) may be calculated by conventional methods, for example according to anyone of the methods according to EP547025, U.S. Pat. No. 5,100,554, EP658352, EP920877 or EP1108438.

To calculate the isoconductive sodium concentration (or the isoconductive sodium concentration related parameter) the conductivity upstream and downstream the filtration unit is measured for the flowing dialysis fluid.

Then an adjusted dialysis fluid having a different concentration of a solute, e.g. sodium, is prepared and the conductivity upstream and downstream the filtration unit is measured again for the adjusted dialysis fluid; for example the two dialysis fluids may differ of about 10 mmol/L.

In other terms, the basic principle of the above described monitoring systems is the continuous measurement of the outlet dialysate conductivity when the inlet dialysate conductivity is changed for example 1 mS/cm during, for example, two (or more) minutes.

Alternatively, the control unit 12 directly receives as an input the isoconductive sodium concentration or plasma conductivity. For example, the physician or the nurse may receive a lab analysis and may provide the datum to the machine through the user interface of the dialysis monitor; the control unit 12 is programmed for storing in a memory 46 the isoconductive sodium concentration or the plasma conductivity to be used for the following dialysis fluid parameter regulation.

In addition, the isoconductive sodium concentration or the plasma conductivity may be estimated using different formulas, not explicitly requiring two dialysis fluids at different sodium concentrations.

For example, according to a further embodiment, the control unit is programmed to calculate the initial plasma conductivity based on the sum of at least the initial conductivity of the dialysate plus a difference between inlet and outlet conductivity at the filtration unit, or dialyzer, weighted by a factor of the dialysate flow rate. In more detail the difference between inlet and outlet conductivity at the filtration unit is weighted by a factor of the blood flow rate in the blood lines too.

Specifically, according to this further embodiment, the control unit 12 is configured to calculate the plasma conductivity using the following formula:

$$\kappa'_{p,1} = \kappa_{0,do} + \frac{Q_{do}}{Q_{Bset}}(\kappa_{0,do} - \kappa_{0,di}) \tag{V}$$

The significance of the denotations above is given in the Glossary.

It is worth to underline that during the above described calculation of the initial plasma conductivity (formula (V)), the dialysis fluid circulates through the secondary chamber 4 maintaining the dialysis fluid parameter value substantially constant.

In an additional embodiment, the control unit 12 is programmed to calculate the initial plasma conductivity based on the sum of at least the initial conductivity of the fresh dialysis fluid plus a difference between inlet and outlet conductivity at the filtration unit weighted by a factor of the dialysate flow rate. In more detail the difference between inlet and outlet conductivity at the filtration unit, or dialyzer, is weighted by a factor of the filtration unit clearance too.

Specifically, according to the additional embodiment, the control unit 12 is configured to calculate the plasma conductivity using the following formula:

$$\kappa''_{p,1} = \kappa_{0,di} + \frac{Q_{do}}{K_u}(\kappa_{0,do} - \kappa_{0,di}) \tag{VI}$$

The significance of the denotations and constants above is given in the Glossary.

It is worth to underline that during the above described calculation of the initial plasma conductivity (formula (VI)), the dialysis fluid circulates through the secondary chamber 4 maintaining the dialysis fluid parameter value substantially constant.

In more detail, in the formulas above $K_u$ is the dialyzer diffusive clearance for urea. Different estimates may be used which are known to the skilled person. $K_u$ may be approximated as $Q_{di}/2$, for example.

Of course, both formulas (V) and (VI) for estimation of plasma conductivity may be iteratively applied, meaning that the newly calculated estimate of PC ($k_{p,1}$) is imposed to the dialysis fluid and a new estimate again calculated after taking measures of the conductivity at the inlet and outlet of the filter as soon as stable conditions are reached.

As previously mentioned, according to an innovative aspect, the control unit 12 receives a value of a parameter. The parameter may be the isoconductive sodium concentration or the isoconductive sodium concentration related parameter.

As mentioned, the control unit 12 is configured for calculating the value of a second parameter of the blood.

The second parameter is chosen between a concentration of a substance in the blood and a concentration-related parameter of a substance in the blood.

Depending on the specific need, the sodium content (or the content of a different electrolyte) in the blood may be determined.

The step of calculating the value of the second parameter of the blood is performed as a function of a main contribution term based on/function of the isoconductive sodium concentration and as a function of an offset contribution term, i.e. a term which takes into account the transport driving gradient of certain specific substances.

The main contribution term may affect (may contribute to) the sodium concentration for at least 80% of the same parameter value (and in particular for at least 90% of the parameter value), i.e. the general value of the sodium concentration in plasma mainly depend on isoconductive sodium concentration.

In more detail, the offset contribution term may contribute to the sodium concentration in blood for less than 20% (or even less than 15%) of the same parameter value (and in particular for less than 10% of the parameter value).

The calculation is a weighted algebraic sum of at least the main contribution term ($c_{di,Na,isocond}$) and the offset contribution term ($C_{di,Na,offset}$) according to the following general formula:

$$c_{p,Na} = \frac{f_{pw}}{\alpha} * (c_{di,Na,isocond} + c_{di,Na,offset}) \quad \text{(VII)}$$

In order to estimate the blood sodium content, i.e. $c_{p,Na}$, an offset factor $C_{di,Na,offset}$, needs to be applied to the isoconductive sodium concentration, i.e. $C_{di,Na,isocond}$.

The main contribution term ($C_{di,Na,isocond}$) is a concentration value which, if used as a dialysis fluid concentration of sodium would run an isoconductive dialysis; we define 'isoconductive dialysis', as a dialysis treatment where the conductivity of the dialysis fluid does not change pre- to post-filtration unit 2, $\kappa_{di}=\kappa_{do}$.

As clear form formula (VII) the concentration of plasma sodium is a weighted sum of $C_{di,Na,isocond}$ and $C_{di,Na,offset}$. In particular the algebraic sum of the two terms is multiplied by a factor $f_{pw}/\alpha$, i.e. the plasma water fraction divided by the Donnan factor.

Though not essential since a calculation may be made based on conductivities too, the main contribution term and the offset contribution term are dimensionally concentrations of a substance (e.g. sodium) in a fluid.

The Applicant has understood that certain specific substances present in the dialysis fluid, namely bicarbonate, potassium, acetate, and citrate have a major effect which should be taken into account when it is desired to estimate the blood sodium content from a measure of isoconductive sodium concentration. Of course other substances play a role, such as lactate, magnesium, and calcium.

Furthermore, the difference in concentration between same substances in the blood and in the dialysis fluid influences, as well, the mentioned estimation.

Given the above, the Applicant also realized that in calculating the offset contribution term, certain parameters having a weight in determining the overload of sodium are known and depends on the machine dressing (e.g. used concentrates) or on the prescription for the patient (e.g. dialysate flow rate). Other parameters depend on the patient undergoing the treatment and therefore may be either directly measured (e.g. lab analysis) or estimated (e.g. based on large population numbers or patient history).

The offset contribution term assumes, in all or almost all prevailing dialysis settings, a negative value, i.e. reduces the main contribution term, this latter being a concentration value which if used as concentration of sodium in the dialysis fluid would allow an isoconductive treatment.

Indeed, the main contribution term takes into consideration the effect of all the ions in causing the isoconductive sodium concentration; the offset contribution term modify this value to determine the sodium (or another substance) concentration only.

In more detail, the control unit is configured to calculate the offset contribution term based on a concentration of at least a substance in the dialysis fluid chosen in the group including bicarbonate, potassium, acetate, lactate, and citrate; in particular calculation is made as a function of the concentration of at least two of said substances, and in further detail as a function of the concentration of bicarbonate, potassium, acetate, and/or citrate, and lactate in the dialysis fluid.

As mentioned, the control unit is configured to calculate the offset contribution term as a function of the weighted difference in concentration of at least one of the above cited substances in the dialysis fluid and the same substances in the blood plasma.

Additionally, the control unit calculates the offset contribution term as a function of the molar conductivities of at least a substance in the dialysis fluid; in detail the substance may be chosen in the group including acids or salts of bicarbonate, chloride, acetate, citrate, phosphate, and sulphate, wherein the salt is formed with sodium, potassium, calcium, and magnesium.

In more detail, the calculations take into account the molar conductivities of at least two of said substances, specifically of at least three and particularly of sodium bicarbonate ($NaHCO_3$), sodium chloride (NaCl), sodium acetate ($NaCH_3COO$), trisodium citrate ($Na_3C_6H_5O_7$), and potassium chloride (KCl).

Again, the offset contribution term is a function of the differences between two molar conductivities, a first molar conductivity of a substance chosen in the group including sodium bicarbonate ($NaHCO_3$), sodium acetate ($NaCH_3COO$), trisodium citrate ($Na_3C_6H_5O_7$), and potassium chloride (KCl), and a molar conductivity of sodium chloride (NaCl).

Alternatively, the offset contribution term is a function of the differences between two molar conductivities, a first molar conductivity of a substance chosen in the group including sodium bicarbonate ($NaHCO_3$), trisodium citrate ($Na_3C_6H_5O_7$), and potassium chloride (KCl), and a molar conductivity of sodium chloride (NaCl).

The control unit is also configured to calculate the offset contribution term as a function of an estimated plasma water concentration of at least a substance chosen in the group including bicarbonate, potassium, acetate, lactate, and citrate; in particular the calculation is made based on the estimated plasma water concentration of at least two, three or four of said substances; in one specific example of the present description the offset contribution term is a function of the estimated plasma water concentration of bicarbonate, potassium, and acetate. In another specific example citrate too is considered.

The estimated plasma water concentration of bicarbonate, potassium, citrate, and acetate is the mean pre-dialysis values of the corresponding substance for large patient populations. The estimated plasma water concentration of bicarbonate, potassium, citrate, and acetate may alternatively be based on other statistical prepared values, or historical values for the specific patient, or direct measurements made before or during the treatment.

Note that, in the specific formula, the estimated plasma water concentration may alternatively be adjusted by a respective (preferably, but not necessarily, fixed) adjusting factor. Numerical values can be e.g. 0.95 ($\alpha$) or 1.05 ($\alpha^{-1}$), but other values may be used (generally depending on the protein content and charge of the ions).

The offset contribution term is an algebraic sum of a plurality of components, a first component being function of the difference, in particular a weighted difference, in concentration of at least a substance in the dialysis fluid and the same substance in the blood plasma, the second component being function of the difference, in particular a weighted difference, in concentration of at least a second substance in the dialysis fluid and the same second substance in the blood plasma, the third component being function of the difference, in particular a weighted difference, in concentration of at least a third substance in the dialysis fluid and the same third substance in the blood plasma.

The substance may be chosen in the group including bicarbonate anions ($HCO_3^-$), acetate anions ($CH_3COO^-$), citrate, and potassium ions ($K^+$), but additionally also lactate.

The above general consideration is reflected in specific and non-limiting implementing formulas which allow, when the isoconductive sodium concentration is known, to determine the precise sodium concentration in the blood.

Of course, different formulas including one or more of the general principles/substances above stated may be alternatively used.

As previously mentioned, in order to estimate the sodium content in blood, i.e. $c_{p,Na}$, an offset factor $C_{di,Na,offset}$ needs to be applied to the calculated isoconductive sodium concentration:

$$c_{p,Na} = \frac{f_{pw}}{\alpha} * (c_{di,Na,isocond} + c_{di,Na,offset}) \quad (VII)$$

where:

$$c_{di,Na,offset} = \quad (II)$$
$$-\frac{1}{M_{\kappa,NaCl}} * [(M_{\kappa,NaHCO_3} - M_{\kappa,NaCl}) * (\alpha^{-1} * c_{pw,HCO_3} - c_{d,HCO_3}) +$$
$$M_{\kappa,KCl} * (\alpha * c_{pw,K} - c_{d,K}) +$$
$$(M_{\kappa,NaAc} - M_{\kappa,NaCl}) * (\alpha^{-1} * c_{pw,Ac} - c_{d,Ac})]$$

Alternatively, in case also the effect of other substances is to be taken into account, the offset factor may be calculated with a similar formula which includes a further term in the algebraic sum.

The further term is a fourth component in the sum depending on at least a ratio between one flow rate, in particular the dialysate flow rate at the outlet of the secondary chamber 4, and an efficiency parameter of the filtration unit 2, in particular a clearance of the filtration unit 2, optionally the urea clearance.

In this case the formula would read:

$$c_{di,Na,offset} = \quad (VIII)$$
$$-\frac{1}{M_{\kappa,NaCl}} * \left[(M_{\kappa,NaHCO_3} - M_{\kappa,NaCl}) * (\alpha^{-1} * c_{pw,HCO_3} - c_{d,HCO_3}) +\right.$$
$$M_{\kappa,KCl} * (\alpha * c_{pw,K} - c_{d,K}) +$$
$$\left.(M_{\kappa,NaAc} - M_{\kappa,NaCl}) * (\alpha^{-1} * c_{pw,Ac} - c_{d,Ac}) + \frac{Q_{do}}{K_u} * (K_{rest1})\right]$$

Factor $\kappa$ (namely, $\kappa_{rest1}$) defines the effect on the conductivity due to other components in the dialysis fluid different from the components already treated and included in the respective formula. Thus, the effect of salts containing calcium, magnesium, lactate, phosphate, and sulphate may have upon the conductivity. The effect created by these components is most often small, and does not vary considerably between the dialysis treatments.

In case citrate is taken into consideration, the formula would read:

$$c_{di,Na,offset} = \quad (IX)$$
$$-\frac{1}{M_{\kappa,NaCl}} * \left[(M_{\kappa,NaHCO_3} - M_{\kappa,NaCl}) * (\alpha^{-1} * c_{pw,HCO_3} - c_{d,HCO_3}) +\right.$$
$$M_{\kappa,KCl} * (\alpha * c_{pw,K} - c_{d,K}) + (M_{\kappa,NaAc} - M_{\kappa,NaCl}) *$$
$$(\alpha^{-1} * c_{pw,Ac} - c_{d,Ac}) + \frac{K_{b_{Cit}}}{K_u}(M_{\kappa_{Na_3Cit}} - 3M_{\kappa_{NaCl}})$$
$$((0.167\alpha^{-3} + 0.125\alpha^{-2} + 0.706\alpha^{-1}) * c_{pw,Na_3Cit} - c_{d,Na_3Cit}) + +$$
$$\left.\frac{Q_{do}}{K_u} * (K_{rest1})\right]$$

$K_{b_{cit}}$ is the approximated clearance value for citrate. This clearance may be calculated for the actual flow rates using a mass transfer value of $K_0A_{cit}=0.212*K_0A_{Urea}$ in the corresponding $K_u$ formula known to the skilled man.

Once the sodium concentration in blood is calculated, the control unit may drive the regulating means 10 for regulating the conductivity or the concentration of the substance in the fresh dialysis fluid and sets the third parameter value for the dialysis fluid in the dialysis fluid supply line 8 at a calculated set point based on the estimated blood sodium content. The third parameter may be the sodium concentration in the dialysis fluid or the conductivity or the same dialysis fluid.

Of course, the estimated blood sodium content may also be used to create a sodium profile in time to be applied to the specific patient in order to control the sodium balance throughout the dialysis treatment.

The invention claimed is:

1. An apparatus for extracorporeal blood treatment comprising:
   a filtration unit having a primary chamber and a secondary chamber separated by a semi-permeable membrane;
   a blood withdrawal line in fluid communication with an inlet of the primary chamber;
   a blood return line in fluid communication with an outlet of the primary chamber, the blood lines being configured for connection to a patient cardiovascular system;
   a dialysis supply line in fluid communication with an inlet of the secondary chamber;
   a dialysis effluent line in fluid communication with an outlet of the secondary chamber; and a control unit programmed to:
receive a first parameter representative of an isoconductive dialysis, the first parameter chosen from a group including: (i) a concentration of a substance; (ii) a concentration-related parameter of the substance; and (iii) a conductivity or conductivity-related parameter,
calculate a second parameter, the second parameter being a concentration or concentration-related parameter of a substance in blood, as a function of a main contribution term based on the first parameter and as a function of an offset contribution term based on a concentration of at least one further substance in the dialysis fluid, the at least one further substance chosen from a group including bicarbonate, potassium, acetate, lactate, citrate, magnesium, calcium, sulphate, and phosphate;
store the second parameter in a memory in communication with the control unit; and
regulate one of (i) a concentration of the substance in the dialysis fluid, or (ii) a conductivity of the dialysis fluid, based on the second parameter,
wherein the main contribution term contributes to at least 80% of the second parameter, and the offset contribution term contributes to less than 20% of the second parameter, and wherein calculating the second parameter as a function of the main contribution term and the offset contribution term is a sub-step of calculating an algebraic sum of at least the main contribution term and the offset contribution term, wherein the offset contribution term is dimensionally a concentration of the further substance in a fluid, and
wherein the control unit is configured to calculate the offset contribution term as a function of a difference in concentration of said further substance in the dialysis fluid and the same further substance in the blood.

2. The apparatus according to claim 1, wherein the control unit is configured to calculate the offset contribution term based on the concentration of two or more further substances in the dialysis fluid chosen from a group including bicarbonate, potassium, acetate, lactate, citrate, magnesium, calcium, sulphate, and phosphate.

3. The apparatus according to claim 1, wherein the control unit is configured to calculate the offset contribution term as a function of a weighted difference in concentration of at least two further substances in the dialysis fluid and the corresponding same further substances in the blood, the further substances being chosen from a group including bicarbonate, potassium, acetate, lactate, and citrate.

4. The apparatus according to claim 1, wherein the first parameter is an isoconductive sodium concentration or isoconductive sodium concentration-related parameter and the second parameter is the concentration of sodium in the blood.

5. The apparatus according to claim 1, wherein the main contribution term is a concentration value which when used as a dialysis fluid concentration of sodium performs an isoconductive dialysis.

6. The apparatus according to claim 1, further including a preparation device for preparing dialysis fluid connected to the dialysis supply line and comprising a regulating device for regulating a composition of the dialysis fluid, the regulating device operated by the control unit.

7. The apparatus according to claim 6, wherein the control unit is configured to set a third parameter for the dialysis fluid in the dialysis supply line at a set point based on the second parameter, the third parameter chosen from a group including (i) a conductivity of the dialysis fluid, (ii) a conductivity-related parameter of the dialysis fluid, (iii) a concentration of at least a substance in the dialysis fluid, and (iv) a concentration-related parameter of at least a substance in the dialysis fluid, wherein the control unit drives the regulating device for regulating the conductivity of the dialysis fluid or the concentration of at least the substance in the dialysis fluid at the set point.

8. The apparatus according to claim 7, wherein the control unit is configured to determine a time profile for a third parameter for the dialysis fluid in the dialysis supply line, the third parameter of the dialysis fluid being chosen from a group including (i) a conductivity of the dialysis fluid, (ii) a conductivity-related parameter of the dialysis fluid, (iii) a concentration of at least a substance in the dialysis fluid, and (iv) a concentration-related parameter of at least a substance in the dialysis fluid, wherein the control unit drives the regulating device for regulating the conductivity or the concentration of at least the substance in the dialysis fluid, the time profile for the third parameter being based on the second parameter.

9. The apparatus according to claim 1, wherein the control unit is configured to calculate the offset contribution term as a function of molar conductivities of one or more further substances in the dialysis fluid chosen from a group including sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$).

10. The apparatus according to claim 1, wherein the control unit is configured to calculate the offset contribution term as a function of a difference between a first molar conductivity of a further substance chosen from a group including sodium bicarbonate ($NaHCO_3$), sodium acetate ($NaCH_3COO$), trisodium citrate ($Na_3C_6H_5O_7$), sodium lactate ($NaC_3H_5O_3$), potassium chloride (KCl), and a molar conductivity of sodium chloride (NaCl).

11. The apparatus according to claim 1, wherein the control unit is configured to calculate the offset contribution term as a function of an estimated or measured plasma water concentration of one or more further substance chosen from a group including bicarbonate, potassium, acetate, lactate, and citrate.

12. The apparatus according to claim 1, wherein the control unit is configured to calculate the offset contribution term as an algebraic sum of at least two components, a first of the components being a function of a concentration of at least one first further substance in the dialysis fluid and/or blood plasma, and a second of the components being a function of a concentration of at least one second further substance in the dialysis fluid and/or blood plasma, wherein the first further substance and second further substance are chosen from a group including bicarbonate anions ($HCO_3^-$), acetate anions ($CH_3COO^-$), citrate anions ($C_6H_5O_7^{3-}$), and potassium ions ($K^+$).

13. The apparatus according to claim 1, wherein the control unit is configured to calculate the offset contribution term as an algebraic sum of at least two components, a first of the components being a function of a weighted difference in concentration of at least one first further substance in the dialysis fluid and the same first further substance in the blood plasma, the second of the components being function of a weighted difference in concentration of at least one second further substance in the dialysis fluid and the same second further substance in the blood plasma, wherein the first further substance and second further substance are chosen from a group including bicarbonate anions ($HCO_3^-$), acetate anions ($CH_3COO^-$), citrate anions ($C_6H_5O_7^{3-}$), and potassium ions ($K^+$).

14. The apparatus according to claim 13, wherein the control unit is configured to calculate an isoconductive sodium concentration as a function of a conductivity of dialysis fluid upstream of the filtration unit, a conductivity of dialysis fluid downstream of the filtration unit, a dialysis fluid flow rate at the inlet of the secondary chamber and an efficiency parameter of the filtration unit.

15. The apparatus according to claim 14, wherein the control unit is configured to determine an isoconductive sodium concentration from at least two conductivity values determined respectively upstream and downstream of the filtration unit in at least two successively prepared dialysis fluids with different concentrations of sodium.

16. An apparatus for extracorporeal blood treatment comprising:
a filtration unit having a primary chamber and a secondary chamber separated by a semi-permeable membrane;
a blood withdrawal line in fluid communication with an inlet of the primary chamber;
a blood return line in fluid communication with an outlet of the primary chamber, the blood lines being configured for connection to a patient cardiovascular system;
a dialysis supply line in fluid communication with an inlet of the secondary chamber;
a dialysis effluent line in fluid communication with an outlet of the secondary chamber; and
a control unit programmed to:
receive a first parameter, wherein the first parameter is an isoconductive sodium concentration or isoconductive sodium concentration-related parameter,
determine a main contribution term based on the first parameter, wherein the main contribution term is a concentration value which, when used as a dialysis fluid concentration of sodium, performs an isoconductive dialysis,
determine an offset contribution term based on:
(i) a concentration of at least one further substance in the dialysis fluid chosen from a group including bicarbonate, potassium, acetate, lactate, citrate, magnesium, calcium, sulphate, and phosphate, and
(ii) a difference between a first molar conductivity of one substance chosen from a group including sodium bicarbonate ($NaHCO_3$), sodium acetate ($NaCH_3COO$), trisodium citrate ($Na_3C_6H_5O_7$), sodium lactate ($NaC_3H_5O_3$), potassium chloride (KCl), and a molar conductivity of sodium chloride (NaCl),
calculate a concentration or concentration-related parameter of sodium in blood as a function of the main contribution term and the offset contribution term,
store the concentration or concentration-related parameter of sodium in blood in a memory in communication with the control unit, and
regulate one of (i) a concentration of the at least one further substance in the dialysis fluid or (ii) a conductivity of the dialysis fluid, based on the concentration or concentration-related parameter of sodium in blood.

17. The apparatus according to claim 16, wherein the control unit is configured to calculate the offset contribution term as a function of a difference in concentration of at least one further substance in the dialysis fluid and the same further substance in the blood, the further substance chosen from a group including bicarbonate, potassium, acetate, lactate, and citrate.

18. The apparatus according to claim 16, wherein the main contribution term affects at least 80% of the second parameter, and the offset contribution term contributes to less than 20% of the second parameter, and wherein calculating the second parameter as a function of the main contribution term and the offset contribution term is a sub-step of calculating an algebraic sum of at least the main contribution term and the offset contribution term, wherein the offset contribution term is dimensionally a concentration of a substance in a fluid.

19. An apparatus for extracorporeal blood treatment comprising:
a filtration unit having a primary chamber and a secondary chamber separated by a semi-permeable membrane;
a blood withdrawal line in fluid communication with an inlet of the primary chamber;
a blood return line in fluid communication with an outlet of the primary chamber, the blood lines being configured for connection to a patient cardiovascular system;
a dialysis supply line in fluid communication with an inlet of the secondary chamber;
a dialysis effluent line in fluid communication with an outlet of the secondary chamber; and
a control unit programmed to:
receive a first parameter, wherein the first parameter is an isoconductive sodium concentration or isoconductive sodium concentration-related parameter,
determine a main contribution term based on the first parameter, wherein the main contribution term is a concentration value which, when used as a dialysis fluid concentration of sodium, performs an isoconductive dialysis,
determine an offset contribution term based on:
(i) a concentration of one or more further substance in the dialysis fluid chosen from a group including bicarbonate, potassium, acetate, lactate and citrate,
(ii) an estimated or measured plasma water concentration of the one or more further substance, and
(iii) molar conductivities of one or more substances in the dialysis fluid chosen from a group including sodium bicarbonate ($NaHCO_3$), sodium chloride (NaCl), sodium acetate ($NaCH_3COO$), potassium chloride (KCl), sodium lactate ($NaC_3H_5O_3$), and trisodium citrate ($Na_3C_6H_5O_7$),
determine a concentration or concentration-related parameter of sodium in blood as a function of the main contribution term and the offset contribution term,
store the concentration or concentration-related parameter of sodium in blood in a memory in communication with the control unit, and
regulate one of (i) a concentration of the one or more further substance in the dialysis fluid and (ii) a conductivity of the dialysis fluid, based on the concentration or concentration-related parameter of sodium in blood.

* * * * *